United States Patent
Slater (10) Patent No.: US 8,337,481 B2
(45) Date of Patent: *Dec. 25, 2012

(54) METHOD FOR TREATING OTITIS EXTERNA

(76) Inventor: Patrick Slater, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,706

(22) Filed: Jun. 8, 2011

(65) Prior Publication Data

US 2011/0263551 A1      Oct. 27, 2011

Related U.S. Application Data

(63) Continuation-in-part of application No. 11/042,542, filed on Jan. 25, 2005, now Pat. No. 7,981,104.

(51) Int. Cl.
*A61M 31/00*      (2006.01)

(52) U.S. Cl. .................................................... 604/514

(58) Field of Classification Search .............. 604/35–43, 604/181, 187, 212, 217, 257, 264, 346, 500, 604/514–517
See application file for complete search history.

(56) References Cited

U.S. PATENT DOCUMENTS

| | | | | |
|---|---|---|---|---|
| 4,278,664 | A | * | 7/1981 | Van Cleave .................. 424/659 |
| 5,843,930 | A | | 12/1998 | Purwar et al. |
| 6,093,417 | A | * | 7/2000 | Petrus .......................... 424/437 |
| 6,350,742 | B1 | | 2/2002 | Costin |
| 6,436,930 | B1 | | 8/2002 | Serrano-Wu et al. |
| 6,440,964 | B1 | | 8/2002 | Cagle et al. |
| 6,509,327 | B1 | | 1/2003 | Cagle et al. |
| 6,521,213 | B1 | | 2/2003 | Mautone |
| 6,706,023 | B1 | | 3/2004 | Huttner et al. |
| 6,723,714 | B2 | | 4/2004 | Hanna |
| 6,764,470 | B2 | * | 7/2004 | Dimick .......................... 604/217 |
| 2002/0013305 | A1 | | 1/2002 | Hanna |
| 2002/0022629 | A1 | | 2/2002 | Cagle et al. |
| 2002/0076383 | A1 | | 6/2002 | Mautone |
| 2003/0045513 | A1 | | 3/2003 | Hanna |
| 2003/0105450 | A1 | | 6/2003 | Dimick |
| 2005/0043251 | A1 | * | 2/2005 | Lane .............................. 514/28 |

OTHER PUBLICATIONS

Emgard et al., "A topical steroid without an antibiotic cures external otitis efficiently: a study in an animal model", Aug. 2001, Eur Arch Otorhinolaryngol. Aug. 2001;258(6):287-91.*

Emgard, P., "A topical steroid without an antibiotic cures external otitis efficiently: a study in an animal model"; www.ncbi.nlm.nih.gov/sites/entres; Apr. 20, 2010; 2 pages.

Emgard and Hellstrom; "A topical steroid without an antibiotic cures external otitis efficiently: a study in an animal model"; Eur Arch Otorhinolaryngol (2001) 258:287-291.

British National Formulary: 12.1.1 Otitis externa; www.bnf.org/bnf/current/doc/5586.htm; 2 pages.

(Continued)

*Primary Examiner* — Matthew F DeSanto
(74) *Attorney, Agent, or Firm* — John A. Fortkort; Fortkort & Houston P.C.

(57) ABSTRACT

A method is provided for treating swimmer's ear and other types of otitis externa. The method comprises (a) diagnosing an instance of swimmer's ear in a patient; and (b) applying to the meatal tissues of the external ear of the patient, in a single application, a volume of a pharmaceutical composition preferably within the range of about 0.1 ml to about 1.5 ml. The pharmaceutical composition comprises a corticosteroid disposed in a viscous medium, and preferably also includes an antifungal agent. The corticosteroid is preferably betamethasone or a betamethasone derivative, and the concentration of the corticosteroid is preferably within the range of about 0.45 mg to about 0.9 mg per gram of the pharmaceutical composition.

26 Claims, 6 Drawing Sheets

OTHER PUBLICATIONS vanBalen, Frank A.M. et al; "Clinical efficacy of three common treatments in acute otitis externa in primary care: randomised controlled trial"; Nov. 22, 2003; PubMed Central; www.pubmedcentral.nih.gov; Jun. 22, 2004; 2 pages.

Infoplease "corticosteroid drug"; www.infoplease.com Jun. 22, 2004; 3 pages.

Corticosteroid converter; www.globalrph.com; Jun. 22, 2004; 1 page.

PDR Drug information for Diprolene (Schering); Drugs.com; www.drugs.com/PDR/Diprolene_Lotion; Sep. 10, 2004; 8 pages.

Schapowal, A., "Otitis externa: a clinical overview"; Ear, Nose & Throat Journal; Aug. 2002; http://articles.findarticles.com; Jun. 22, 2004; 4 pages.

Waitzman, Ariel A., "Otitis Externa"; eMedicine, www.emedicine.com; updated Nov. 28, 2001; 11 pages.

The Healthcare Sales & Marketing Network News Release Jul. 21, 2003; "Alcon Receives FDA Approval for Novel Combination Ear Infection Treatment"; http://salesandmarketingnetwork.com; 2 pages.

HON Allergy Glossary Corticosteroid; www.hon.ch/Library/Theme/Allergy/Glossary/corticosteroid.html; Jun. 22, 2004; 2 pages.

Otitis externa (Ear Canal Infection); xtramsn; www.xtramsn.co.nz/health; Jun. 22, 2004; 5 pages.

Sander, Robert; "Otitis Externa: A Practical Guide to Treatment and Prevention"; American Academy of Family Physicians; Mar. 1, 2001; www.aafp.org; 10 pages.

\* cited by examiner

METHOD FOR TREATING OTITIS EXTERNA

RELATED APPLICATIONS

The present application is a continuation-in-part and claims priority to U.S. Ser. No. 11/042,542, which is entitled "Method for Treating Otitis Externa", which was filed on Jan. 25, 2005 now U.S. Pat. No. 7,981,104, and which is incorporated herein by reference in its entirety.

TECHNICAL FIELD OF THE INVENTION

The present invention pertains generally to treatments for otic infections, and more specifically to treatments for otitis externa that utilize corticosteroids.

BACKGROUND OF THE INVENTION

Otitis externa is a disease of the external ear that is characterized by inflammation of the meatal skin. Over 90% of cases of otitis externa can be traced to bacterial and/or fungal infections. In the incipient stage, symptoms of otitis include itching and pain in the ear canal, often accompanied by tenderness in the area around the external auditory meatus and pain when the ear lobe is pulled or when the jaw is moved. In the definitive stage, suppuration occurs in the ear canal, and may be accompanied by decreased auditory function. Treatment of otitis externa is complicated by the relative inaccessibility of the infected meatal skin, which makes it difficult to effectively apply a treatment to the affected area.

One of the most common types of otitis externa encountered by physicians is a type designated as "swimmer's ear". Swimmer's ear has long been understood in the medical arts to be an infection of bacterial etymology, and is treated accordingly. Hence, current medical practice for the treatment of swimmer's ear prescribes a multiple dose, antibiotic ear drop regiment for the treatment of this condition. In some cases, these drops may include a small dosage of a steroid or an organic acid, such as acetic acid. Typically, the ear drops are applied to the infected ear two times a day for 10 days. This approach is consistent with standard medical practice in the treatment of bacterial infections, which seeks to eradicate the causal bacteria by (a) utilizing daily dosing so as to maintain a high level of an antibiotic in the patient's bloodstream, and (b) maintaining local contact over an extended period of time.

While an eardrop regimen may be an effective treatment for swimmer's ear in some cases, and offers the considerable convenience of being able to be administered by the patient, any interruption of the treatment which results in missed dosages or applications may result in failure to cure the disease. Moreover, the topical application of eardrops often results in inadequate physical contact with the surfaces to be treated, and even when proper contact is made, such contact may be of an insufficient duration to achieve the desired physiological effect. Moreover, current eardrop formulations are found to be ineffective in a significant number of cases, even if they are properly administered.

The effectiveness of an eardrop regimen, or of any other treatment requiring periodic application of a pharmaceutical composition, can often be optimized when practiced by a skilled physician. However, as a practical matter, many patients are unwilling to participate in treatments that require multiple visits to a hospital or healthcare provider. Consequently, a number of such patients avoid initial treatment or follow-up treatments, with the result that a readily curable condition of otitis externa matures into a more acute condition requiring serious medical intervention. A similar result may occur if there is any significant delay between the occurrence of the initial symptoms and subsequent treatment, as a result of, for example, a delay in scheduling an office visit. In this respect, it is notable that the growth rate of infecting organisms in diseased tissues is often exponential.

Alternative methods have been developed in the art for treating swimmer's ear and other types of otitis externa, frequently with an object of overcoming one or more of the aforementioned infirmities. Some of these treatments may be used in conjunction with an eardrop regimen. For example, one approach involves introducing into the infected area a ribbon gauze dressing soaked with antibacterial ear drops (the ear drops may contain a small dosage of a steroid) or with an astringent such as aluminum acetate solution. While such an approach may be very effective in some cases, it is not practical in many of the more acute instances of otitis externa, since contact between the inserted gauze and the inflamed meatal tissues can be extremely painful. Moreover, this approach cannot be administered by the patient, and hence requires the patient to visit a physician for the treatment.

There is thus a need in the art for a method for treating otitis externa which does not require multiple applications, which is ameniable to treatment without delay, and which is effective in treating swimmer's ear and other types of otitis externa. There is further a need in the art for a method for treating otitis externa which is non-invasive, which can be administered by the patient, and which effectively contacts the infected meatal skin. These and other needs are met by the devices and methodologies disclosed herein and hereinafter described.

SUMMARY OF THE INVENTION

In one aspect, a device for treating otitis externa is provided herein. The device comprises a receptacle adapted to store a pharmaceutical composition; a distal portion in open communication with said receptacle, said distal portion being adapted to apply the composition disposed in said receptacle to the meatal tissues of the external ear; and a pharmaceutical composition disposed in said receptacle, said pharmaceutical composition comprising a corticosteroid disposed in a viscous medium. In some embodiments, the composition further includes an antifungal agent.

In another aspect, a method for treating otitis externa is provided herein. In accordance with the method, an applicator is provided which is equipped with a reservoir for storing a pharmaceutical composition comprising a corticosteroid disposed in a viscous medium (in some embodiments, the composition further includes an antifungal agent), and a distal portion, in open communication with said body, which is adapted to apply the pharmaceutical composition to the meatal tissues of the external ear. The applicator is then utilized to apply the contents of the reservoir to the meatal tissues of the external ear.

In yet another aspect, a method for treating otitis externa is provided, which comprises the steps of (a) receiving a communication from a patient indicating a possible case of otitis externa; (b) prescribing a single dosage treatment for the patient of a pharmaceutical composition comprising a corticosteroid disposed in a viscous medium (in some embodiments, the composition further includes an antifungal agent); and (c) scheduling an office visit with the patient.

In a further aspect, a method for treating swimmer's ear is provided. The method comprises (a) diagnosing an instance of swimmer's ear in a patient; and (b) applying to the meatal tissues of the external ear of the patient, in a single application, a volume of a pharmaceutical composition within the range of about 0.1 ml to about 1.5 ml; wherein said pharmaceutical composition comprises a corticosteroid disposed in a viscous medium, alone or in combination with an antifungal agent; wherein the corticosteroid is betamethasone or a betamethasone derivative, and wherein the concentration of the corticosteroid is within the range of about 0.45 mg to about 0.9 mg per gram of the pharmaceutical composition.

One skilled in the art will appreciate that the various aspects of the present disclosure may be used in various combinations and sub-combinations, and each of those combinations and sub-combinations is to be treated as if specifically set forth herein.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

It has now been discovered that swimmer's ear is not a bacterial infection as supposed by existing medical practice, but is instead a fungal dermatitis of varying degrees of virulence. In light of this discovery, a new treatment for swimmer's ear has been developed, and is described herein, which properly accounts for the fungal etymology of the disease. This approach, which is also effective in the treatment of some other types of otitis externa, preferably utilizes a single application of a pharmaceutical composition to the infected meatal tissues. The composition preferably comprises a pharmaceutically effective amount of a corticosteroid and an antifungal agent disposed in a viscous or gelatinous medium. In some embodiments, the composition may further include an antibacterial agent. The treatment preferably uses the occlusive effect inherent in the application of the composition to the ear canal to achieve effective contact with the meatal tissues for a sufficient duration of time.

In an especially preferred embodiment, the treatment involves a single application of an ointment to the ear which utilizes betamethasone and clotrimazole as the active ingredients. Clotrimazole is an antifungal medication presently used in the treatment of some fungal infections, such as vaginal yeast infections. Betamethasone is a glucocorticoid steroid with anti-inflammatory and immunosuppressive properties. Preferably, the composition is devoid of an antibiotic.

In the preferred embodiment, the initial dosage of corticosteroid in the composition is high. For example, in the case of betamethasone, the total amount of corticosteroid administered is preferably within the range of about 0.45 to about 0.9 mg. The composition may be applied with the use of an applicator containing therein a pre-metered dosage of the pharmaceutical composition. The applicator ensures proper application of the correct amount of corticosteroid to the meatal tissues.

Without wishing to be bound by theory, it is believed that the application of a single high dosage composition of a corticosteroid is very effective in treating otitis externa, at least in part due to its ability to rapidly reduce swelling in the external ear. The reduction in swelling permits the infected tissues to be more easily contacted with the bacterial, antifungal and/or pH reducing agents which may be included in the composition. Moreover, the inclusion of an antifungal agent in the composition allows it to be used to effectively treat swimmer's ear, by effectively addressing the underlying etymology of the disease. In addition, the use of a viscous medium within the composition ensures that the composition remains in contact with the infected tissues long enough for effective treatment, since the adsorption of corticosteroids in a topical application is typically a transdermal phenomenon.

A system for treating otitis externa is also provided herein which makes advantageous use of the aforementioned pharmaceutical compositions. In accordance with this method, a physician receives a phone call or other communication from a patient indicating a possible case of otitis externa. The physician then prescribes a single, preferably high dosage treatment for the patient of the pharmaceutical composition described above. An office visit with the patient is scheduled, either prior to, contemporaneous with, or subsequent to the issuance of the prescription. This system is advantageous in that it provides for early treatment of the disease, and thus minimizes the discomfort of the patient. Moreover, the application of a single high dosage treatment, in combination with a treatment that lends itself to application by the user, helps to ensure that the infection will not advance prior to the patient's next office visit. This system may also leverage digital imaging devices and other such technology to facilitate a preliminary diagnosis prior to an office visit.

Figure 1:
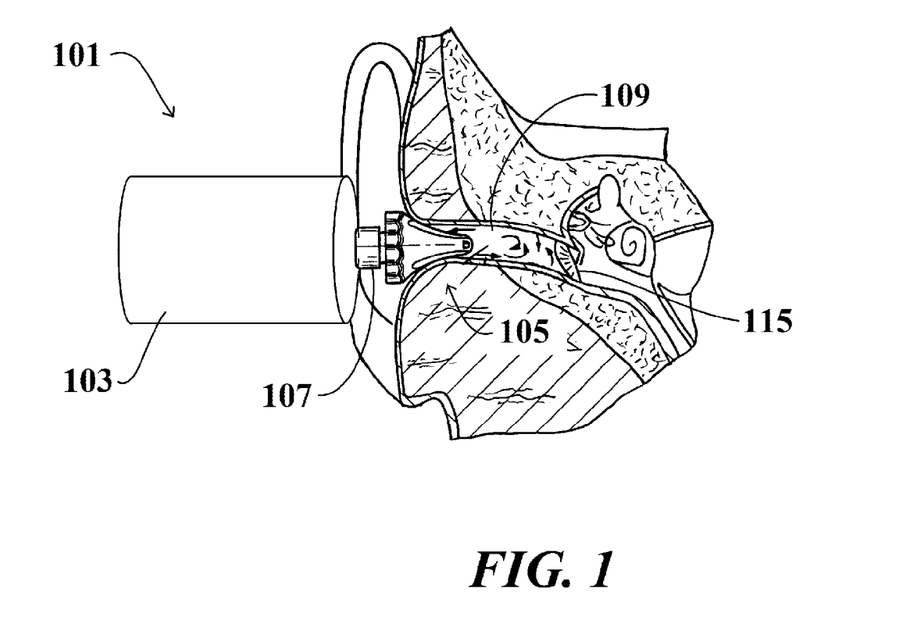
FIG. 1 is an illustration of the use of a first embodiment of an applicator in the administration of the pharmaceutical compositions described herein.
Figure 2:
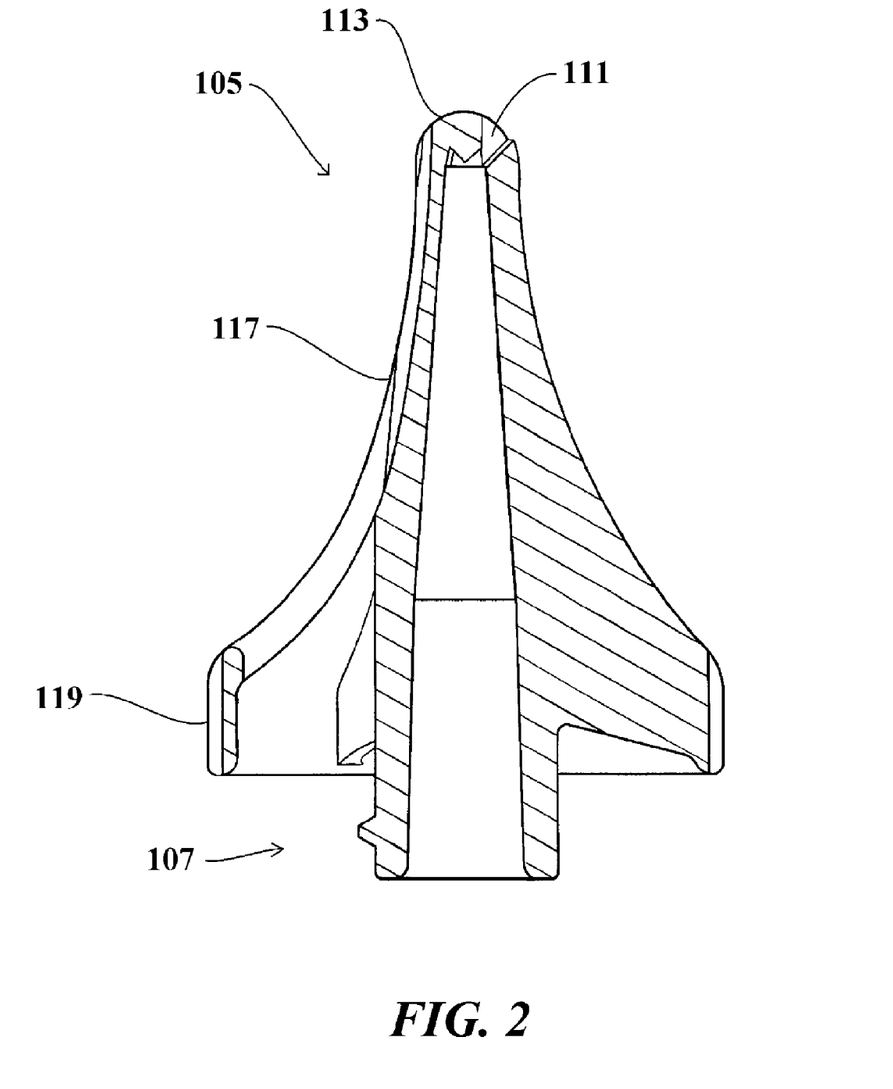
FIG. 2 is a cross-sectional view of the distal portion of the applicator of FIG. 1.

FIG. 1 illustrates one particular, non-limiting example of a means by which the pharmaceutical composition of the present invention may be applied to the external ear of a patient. As shown therein, an applicator 101 is provided which contains the pharmaceutical composition. The applicator consists of a receptacle 103 which, when the applicator is in an open position, is in open communication with a distal portion 105 via a neck 107. The distal portion, which in some embodiments can be made essentially complimentary in shape to the ear canal 109, has at least one, and preferably a plurality of, openings 111 (see FIG. 2) in the tip 113 thereof through which the composition can be dispensed. The receptacle, which may assume a number of shapes and configurations, is sufficiently deformable to allow the contents of the vessel to be dispensed through the plurality of openings through normal hand pressure when the applicator is in an open position. The interior surface of this receptacle will typically be selected to be inert to the pharmaceutical composition disposed within the receptacle.

The distal portion 105 of the applicator is preferably equipped with positioning means or features for ensuring the proper positioning of the tip 113 within the ear canal 169 of the user. Such a positioning means prevents the tip 113 of the applicator from advancing too far into the ear canal 109, where it could cause damage to the ear drum 115, but also ensures that the tip penetrates the ear canal sufficiently to ensure sufficient contact between the pharmaceutical composition and the meatal tissues. In the particular embodiment depicted in FIG. 1, the positioning means or features are in the form of a tapered shaft 117 which extends from the tip 113 and terminates in an annular portion 119 that is appropriately patterned to provide suitable finger grip. In other embodiments, however, the distal portion 105 may have less of a taper, and the positioning means may comprise only the annular portion 119.

In some embodiments, the distal portion of the applicator may be constructed such that it is rotatable about an axis from a first position in which the distal portion is in closed communication with the receptacle, to a second position in which the distal portion is in open communication with the receptacle. This facilitates the sanitary storage of the pharmaceutical composition, and facilitates application of the composition by the user.

Figure 3:
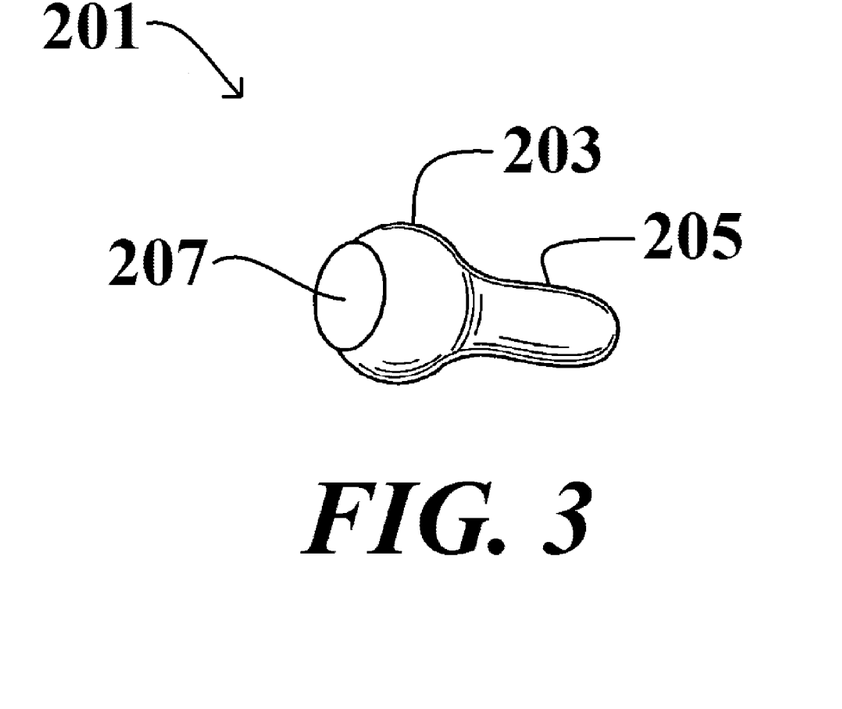
FIG. 3 is an illustration of a second embodiment of an applicator useful for the administration of the pharmaceutical compositions described herein.
Figure 4:
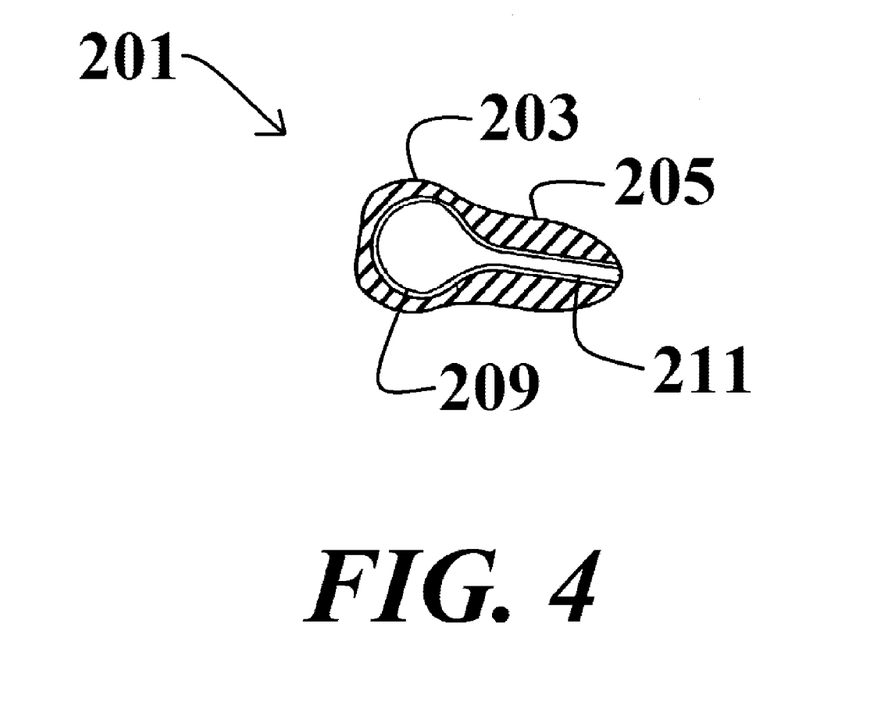
FIG. 4 is a cross-sectional illustration of the applicator of FIG. 3 taken along the LINE 4-4.
Figure 5:
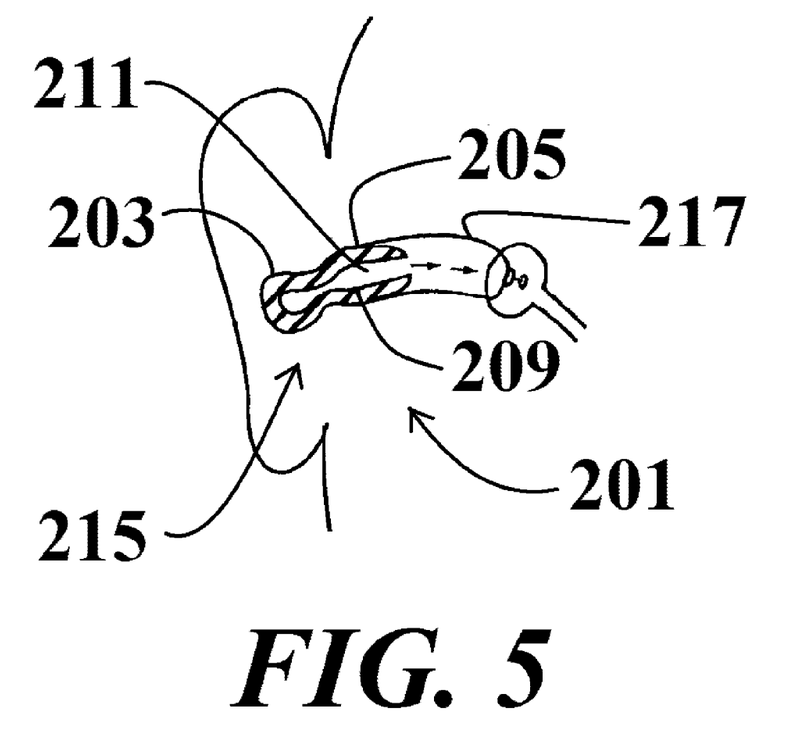
FIG. 5 is an illustration of the use of the applicator of FIG. 3 in the administration of the pharmaceutical compositions described herein.

Referring now to FIGS. 3-5, a second particular, non-limiting embodiment of an applicator is depicted which is useful for the application of pharmaceutical compositions in accordance with the teachings herein. In this embodiment, the applicator 201 is in the form of a unitary plug having a bulbous portion 203 which is in open communication with a distal portion 205. A cap 207 may be provided in the bulbous portion to provide access to the interior chamber 209 or reservoir thereof for the purpose of charging the chamber. This cap may be provided with a string to facilitate removal of the applicator from the ear canal. As seen in FIG. 4, the interior chamber 209 is in open communication with the distal portion 205 via a central channel 211. As indicated in FIG. 5, the bulbous portion of the applicator is sufficiently deformable through the application of normal hand pressure such that, when the applicator is positioned within the ear canal and normal finger pressure is applied, the pharmaceutical composition may be driven out of the interior chamber 209, through the central channel 211, and out of the tip 213, where it comes into contact with the meatal tissues.

The tip of the applicator may be provided with a removable stopper (not shown), which may take the form of a pin that extends into the central channel 211 from the exterior of the device and prevents contamination of the pharmaceutical composition or premature expulsion of the composition. In use, the stopper would be removed just prior to application of the composition to the external ear 215 of the patient in the manner depicted in FIG. 5.

The dimensions of the bulbous portion 203 and distal portion 205 of the applicator are preferably selected such that the distal portion is readily insertible into the ear canal 217, is preferably somewhat complimentary in shape thereto, and extends sufficiently far into the ear canal 217 to allow for the proper administration of the pharmaceutical composition, but not so far as to allow contact between the tip 213 of the distal portion and the patient's ear drum. The bulbous portion 203 is preferably sufficiently large to store the desired amount of the pharmaceutical composition in the interior chamber 209 thereof and to prevent the tip 213 of the distal portion 205 from advancing too far into the ear canal 217.

Various corticosteroids may be used in the devices and methodologies disclosed herein. These include, for example and without limitation, cortisone, cortisol, hydrocortisone, methylprednisolone, prednisolone, prednisone, triamcinolone, betamethasone, and dexamethasone. Various esters and other derivatives or salts (including hydrates and hydrogen chloride salts) of the foregoing may also be employed. Also, various combinations or sub-combinations of the aforementioned materials may be used.

The amount of steroid in the compositions described herein may vary and, in some cases, may be selected or adjusted in consideration of the patient's status, sensitivity to the steroid in question, the biologic half-life of the steroid, the patient's age, systemic tolerances of the steroid, and other such factors. Preferably, however, the compositions described herein are prepared so that they are suitable for administration to large groups or classes of patients. For example, the compositions may be made available in a small number of pre-metered dosages that are suitable for administration to certain predefined groups (for example, the compositions may be prepared in two formulations, with one formulation suitable for use with children and another formulation suitable for use with adults).

The specific dosage of steroid in the compositions described herein will vary depending on the particular steroid employed. Typically, however, the relative dosage of steroid will decrease with increasing half-life of the steroid, since corticosteroids can have systemic effects that should be considered in determining dosages. TABLE 1 below indicates some possible ranges for the dosages of various steroids in the compositions described herein. This table assumes the use of a single steroid in the composition. One skilled in the art will appreciate that these dosages may be suitably modified to account for pharmaceutical compositions containing two or more of these steroids.

TABLE 1

Dosage Ranges (in mg per gram of steroid composition)

| Steroid | Dosage Range | Preferred Dosage Range | More Preferred Dosage Range | Most Preferred Dosage Range | Biological Half Life (Hours) |
|---|---|---|---|---|---|
| cortisone | 12-50 | 19-31 | 22-28 | 25 | 8-12 |
| hydrocortisone | 10-40 | 15-25 | 18-22 | 20 | 8-12 |
| Methyl-prednisolone | 2-8 | 3-5 | 3.6-4.4 | 4 | 18-36 |
| prednisolone | 2.5-10 | 3-5 | 4.5-5.5 | 5 | 18-36 |
| triamcinolone | 2-8 | 3-5 | 3.6-4.6 | 4 | 18-36 |
| Betamethasone | 0.3-1.5 | 0.45-0.9 | 0.54-0.83 | 0.6-0.75 | 36-54 |
| dexamethasone | 0.3-1.5 | 0.56-0.94 | 0.69-0.83 | 0.75 | 36-54 |

It is to be noted that these steroids may be administered as salts or derivatives of the parent steroid. For example, betamethasone is frequently administered as betamethasone dipropionate (which has the chemical name 9-fluoro-11β,17,21-trihydroxy-16β-methylpregna-1,4-diene-3,20-dione17, 21-dipropionate, which has an empirical formula of $C_{28}H_{37}FO_7$, and which has a molecular weight of 504.59 g/mol), and the dosage given for betamethasone in TABLE 1 is based on this particular salt.

The concentration of corticosteroid in the pharmaceutical compositions made in accordance with the teachings herein may vary. Preferably, however, this concentration is selected based on such considerations as the total amount of the pharmaceutical composition that it is desired to apply to the meatal tissues, and the stability or shelf life of the steroid or other ingredients of the pharmaceutical composition as a function of concentration. Typically, the total amount of the pharmaceutical composition applied to a patient is at least about 0.05 cc, preferably about 0.1 to about 4 cc, more preferably about 0.5 to about 3 cc, and most preferably about 1 cc to about 2 cc.

As previously noted, the use of a single, high dosage of a corticosteroid in the methodology described herein is very effective in rapidly reducing swelling in infected meatal tissues, which allows better access to, and treatment of, these tissues. Preferably, these compositions further comprise an antibacterial, antifungal and/or pH adjusting agent, since fungi and bacteria are implicated in the vast majority of cases of otitis externa, and since a pH of less than about 6 is disadvantageous to the growth of bacteria typically encountered in otitis externa. Hence, inclusion of these agents may, in some cases, allow for elimination of the original cause of the disease.

Various anti-bacterial agents may be used in the pharmaceutical compositions described herein. These include, but are not limited to, flucloxacillin, triclosan (2,4,4'-Trichloro-2'-hydroxydiphenyl ether), alcohols (including ethanol and isopropyl alcohol), peroxides (including benzoyl peroxide), iodine, benzethonium chloride, chloroxylenol and aminoglycoside antibiotics such as ciprofloxacin. Various derivatives or salts (including hydrates and hydrogen chloride salts) of the foregoing may also be employed. Also, various combinations or sub-combinations of the aforementioned agents may be employed. The anti-bacterial agents may be selected on the basis of their bacteriostatic activity against gram-negative and/or gram-positive bacteria, and are preferably selected to combat the bacteria commonly implicated in otitis externa, including staphylococci, streptococci, pseudomonas, or *Escherichia coli*. The anti-bacterial agent may also be selected based on a particular species of bacteria known to be present in the infected tissue, as determined by biopsy or by other means.

Various anti-fungal agents may be used in the pharmaceutical compositions described herein. These may include, but are not limited to, natamycin, ciclopirox, clotrimazole, econazole, miconazole, nystatin, oxiconazole, terconazole, and tolnaftate. The anti-fungal agents may be selected to combat fungi commonly implicated in otitis externa, including *aspergillus* and *candida* fungi.

As previously noted, it is preferred that the pharmaceutical compositions described herein are sufficiently viscous that they maintain contact with the meatal tissues of the external ear for a sufficient amount of time to provide effective treatment of those tissues. On the other hand, it is also preferred that these compositions have a low enough viscosity so as to permit their administration using the types of applicators described herein. Typically, the pharmaceutical composition will be designed to have a viscosity well above that of water at room temperature (water has a viscosity of 1 centipoise at 70° F.), and more typically will have a viscosity of greater than 200 centipoise at room temperature. Preferably, the room temperature viscosity of the composition will be within the range of 200 to 110,000 centipoise, more preferably within the range of 200 to 80,000 centipoise, even more preferably within the range of 3,000 to 70,000 centipoise, and most preferably within the range of 20,000 to 64,000 centipoise. To this end, various viscosity enhancing or modifying agents may be used in the pharmaceutical compositions described herein. These include, but are not limited to, such materials as methylcellulose, polyvinyl alcohol, and glycerin.

Various preservatives may also be used in the pharmaceutical compositions described herein to increase the shelf life of these compositions. These preservatives may include, but are not limited to, such materials as potassium sorbate, sodium benzoate, benzyl alcohol, and various combinations or sub-combinations of the foregoing.

Various solvents, carriers, and/or media may also be used in the pharmaceutical compositions described herein. These include, but are not limited to, various carboxylic acids and alcohols.

Various topical analgesics may also be used in the pharmaceutical compositions described herein. These include, but are not limited to, paracetamol and other suitable analgesics.

Various other materials may be used in the pharmaceutical compositions described herein. These include, but are not limited to, astringents such as aluminum acetate, and topical anti-infectives such as neomycin, clioquinol, or chloramphenicol.

The pharmaceutical compositions described herein will preferably have a pH of less than about 6, since the use of compositions having higher pHs may promote, or inadequately discourage, the growth of bacteria in the meatal tissues. In some cases, the specific pH, or range of pHs, prescribed for the pharmaceutical composition may depend on the particular corticosteroid, or combination of corticosteroids, chosen for the composition, since pH can have an effect on the solubility and/or shelf life of these materials.

The pharmaceutical compositions, and the methodologies for their application, will now be described with reference to the following non-limiting examples.

EXAMPLE 1

This example demonstrates the make-up of a particular, non-limiting embodiment of a composition useful in treating otitis externa in accordance with the methodologies described herein.

A pharmaceutical composition in the form of a cream was prepared. The composition contained, as the active ingredient, betamethasone dipropionate, a synthetic adrenocorticsteriod which is an analog of prednisolone (betamethasone dipropionate is the 17,21-dipropionate ester of betamethasone). Betamethasone dipropionate has the empirical formula $C_{28}H_{37}FO_7$ and a molecular weight of 504.6, and possesses the following structural formula:

The cream contained the following ingredients (the amount of steroid is per gram of cream):

betamethasone dipropionate (0.643 mg);
purified water;
isopropyl alcohol (30%);
hydroxypropyl cellulose;
propylene glycol;
sodium phosphate monobasic monohydrate; and
phosphoric acid.

The amount of phosphoric acid added was sufficient to adjust the pH of the composition to 4.5.

EXAMPLE 2

This example demonstrates the make-up of a particular, non-limiting embodiment of a composition useful in treating otitis externa in accordance with the methodologies described herein.

A pharmaceutical composition in the form of a gel was prepared. The composition contained betamethasone dipropionate as the active ingredient, and further contained the following ingredients (the amount of steroid is per gram of cream):

- betamethasone dipropionate (0.643 mg);
- purified water;
- chlorocresol;
- propylene glycol;
- white petrolatum;
- white wax;
- cyclomethicone;
- sorbitol solution;
- glyceryl oleate/propylene glycol;
- ceteareth-30;
- carbomer 940; and
- sodium hydroxide.

EXAMPLE 3

This example demonstrates the make-up and dosage of a particular, non-limiting embodiment of a composition useful in treating otitis externa in accordance with the methodologies described herein.

A gel was prepared which contained betamethasone dipropionate as the active ingredient disposed in an augmented gel base. The gel had the following composition (the amount of steroid is per gram of gel):

- betamethasone dipropionate (0.643 mg);
- carbomer 940;
- propylene glycol;
- purified water; and
- sodium hydroxide.

Separately, a cream was prepared which contained clotrimazole as the active ingredient disposed in a vanishing cream base. The cream had the following composition (the amount of clotrimazole, an antifungal agent, is per gram of gel):

- clotrimazole (10 mg);
- sorbitan monostearate;
- polysorbate 60;
- cetyl esters wax;
- cetostearyl alcohol;
- 2-octyldodecanol;
- purified water; and
- benzyl alcohol (1%).

The gel and the cream were combined in a 1:1 ratio by volume to yield the final (gelatinous) pharmaceutical composition. The resulting composition is preferably applied in a dosage of 1-2 cc of the total composition, thus involving the application of about 0.5-1 cc of the betamethasone dipropionate gel. Most preferably, a dosage of about 2 cc of the pharmaceutical composition (containing 0.5 cc of the betamethasone dipropionate gel) is applied.

EXAMPLE 4

This example demonstrates the efficacy of the methodologies described herein in treating otitis externa.

The composition of EXAMPLE 3 was applied in a single dose to the meatal tissues of several test subjects suffering advanced cases of otitis externa. In each case, a dosage of approximately 2 cc (about 0.32 mg of the corticosteroid betamethasone dipropionate) of the pharmaceutical composition was applied to the external ear by syringe to test the efficacy of the treatment. Some of these subjects had previously been treated with a regiment of ear drops or other treatments, but had not responded to the therapy. Other subjects were receiving treatment for the first time. The subjects were of various ages and physical condition.

In greater than 95% of the cases, the subjects responded favorably to the treatment, with a noticeable improvement in the state of the meatal tissues and a reduction or elimination of associated symptoms.

Figure 6:
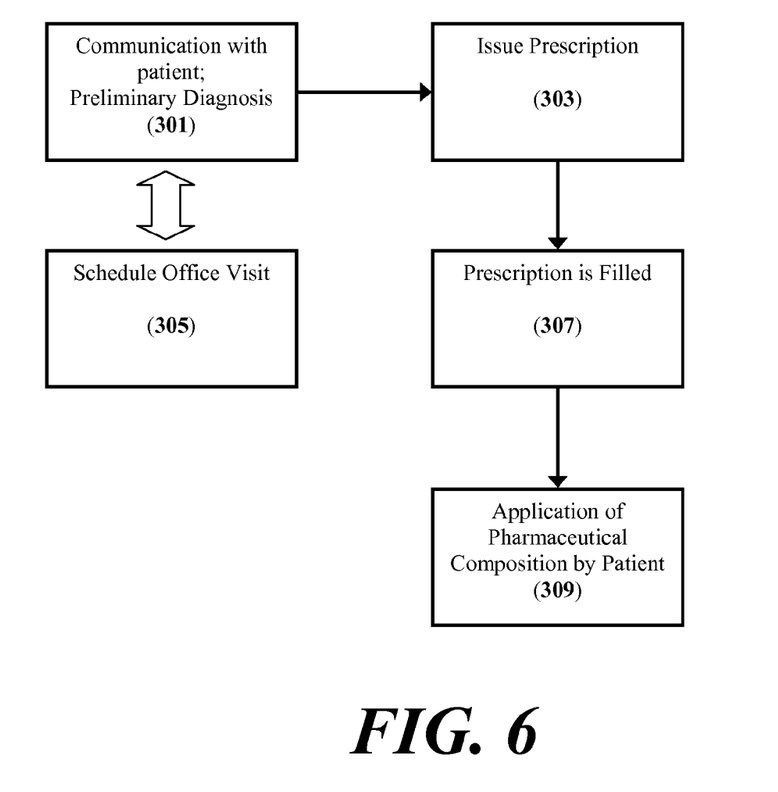
FIG. 6 is a flowchart illustrating a method for treating otitis externa in accordance with the teachings herein.

The pharmaceutical compositions and devices described herein may be utilized as part of an early treatment procedure for potential cases of otitis externa. One non-limiting embodiment of such a treatment procedure is illustrated in FIG. 6. As shown therein, an otolaryngologist, physician or other health care professional receives 301 a communication from a patient, or prospective patient, implicating a possible case of otitis externa. The communication will most typically be in the form of a telephone call, but may also be in the form of an email, facsimile, voice message, or through other suitable means. In some cases, the communication may include digital images of the infected area.

The health care professional then prescribes 303 treatment of the condition with one of the pharmaceutical compositions described herein. This step will typically involve transmitting the prescription, through any of the means known to the art, to a pharmacy or other agent suited to fill the prescription. The methodology also contemplates variations in which the prescription is issued by a person other than the person receiving the communication from the patient. Either before or after issuing the prescription, the health care professional, or the health care professional's support staff, schedules 305 an office visit with the patient to assess the status of the infection and/or the efficacy of the treatment.

The patient then has the prescription filled 307, which will typically involve obtaining from a pharmacy or other agent an applicator charged with the pharmaceutical composition. The patient then uses this applicator to apply 309 the appropriate amount of the pharmaceutical composition to his or her external ear. Preferably, the amount of the pharmaceutical composition in the applicator is pre-metered, and the patient is instructed to apply the complete contents of the applicator to the patient's external ear.

Several variations to the aforementioned methodology are possible. For example, the applicators and other devices described herein for the application of the pharmaceutical composition, while capable of being used by the patient without supervision by the health care professional, may also be used during an office visit or surgical consultation, either by an otolaryngologist or by a nurse or other health care professional. These devices are especially useful when the health care professional applying the composition is not a trained otolaryngologist, since the "fool-proof" nature of these devices can compensate somewhat for lack of experience or skill in applying these compositions. Moreover, since these devices can be charged with a pre-metered dosage of the pharmaceutical composition, there is a lessened danger of over-dosage or under-dosage. Of course, it will be appreciated that a trained otolaryngologist or a health care professional experienced in applying pharmaceutical compositions to the meatal tissues can also apply the pharmaceutical compositions described herein by way of a syringe or through the use of other known and suitable devices.

Moreover, while the devices, methodologies and compositions disclosed herein have been described primarily with reference to their application to humans, one skilled in the art will appreciate that they have a variety of other uses. In particular, the devices, methodologies and compositions disclosed herein have many applications in the veterinary arts. It will be appreciated that, in such applications, features such as the dosage and the size or type of applicator used may vary, and will be selected with the intended subject in mind.

The compositions and methodologies disclosed herein are particularly suitable for the treatment of swimmer's ear, chronic external otitis and otomycosis, they may also be applied to the treatment of various other types of otitis externa. In this respect, it is to be noted that the term otitis externa is a general descriptive term and is not a specific diagnosis. Generally, otitis externa is an infection of the external ear, which has many causes. It is generally accompanied by redness, swelling and pain of the ear canal and pinna, and often causes the tympanic membrane to become dull or red. There is usually some form of drainage or exudates associated with otitis externa. Otitis externa encompasses the following distinct maladies:

1—Acute diffuse bacterial external otitis (swimmers ear)
2—Acute localized external otitis (furunculosis)
3—Impetigo of the external ear
4—Erysipelas
5—Perichondritis
6—Chronic external otitis
7—Otomycosis
8—Malignant otitis externa
9—Herpes
10—Tube Otorrhea
11—Cholesteatome
12—Otitis Media with Perforation Each of these will be briefly described in turn. A more detailed discussion of these conditions may be found in Cummings, "Otolaryngology: Head & Neck Surgery", 5th ed. (2010).

Acute diffuse bacterial external otitis is a type of otitis externa most commonly caused by the bacteria pseudomonas and *staphylococcus*. The diagnosis is made by exam and bacterial cultures. Conventional treatment is with aural hygiene and topical drops.

Acute localized external otitis (furunculosis) is a form of otitis externa caused by the infection of secretory glands in the ear canal. The diagnosis is made by examination with a localized pointing lesion. Conventional treatment typically involves the use of topical antibiotics, debridement, and oral antibiotics.

Impetigo of the external ear is a type of otitis externa manifested as a localized area of infection caused by trauma, as, for example, by abrasion with a fingernail. Bacteria are the causative agent and are conventionally treated by debridement of the area and by topical antibiotics.

Erysipelas is a type of otitis externa arising from strep cellulites of unknown cause. This is a more diffuse infection of bacterial origin, and is conventionally treated with oral antibiotics. Chills and fever are common, and the patient typically appears more acutely ill.

Perichondirtis is a type of otitis externa arising from a bacterial infection of the cartilage of the ear canal and auricle. The cause may be autoimmune or bacterial. Conventional treatment is through surgical debridement and IV antibiotics.

Chronic external otitis is a type of otitis externa manifested as an edema of the ear canal. Treatment is difficult, though in some cases, the use of topical steroids has been found to be effective.

Otomycosis is a type of otitis externa present as an infection of fungal etymology, with cultures at times showing a mixed infection of bacteria and yeast. In the absence of hyphae or other diagnostic features, a KOH preparation of superficial scraping from the canal wall may yield the diagnosis. Otomycosis is conventionally treated through debridement and the use of topical agents to change the PH of the ear canal.

Malignant otitis externa is a type of otitis externa manifested as a severe, life threatening infection of the ear canal, bone and skull. Conventional treatment requires topical antibiotics, IV antibiotics and, at times, extensive surgical debridement. Correction of the underlying medical condition (usually diabetes) is also indicated. This diagnosis has a high morbidity and mortality rate associated with it.

Herpes infection is a type of otitis externa manifested as vesicular lesions of the ear canal and auricle. It is caused by viral infection, and is conventionally treated with oral antiviral agents and local cleaning of the ear canal and auricle.

Tube otorrhea is a type of otitis externa associated with pressure equalization tube insertion. After the tube is inserted, there is commonly granulation tissue and other causes of otorrhea from the tube which can give rise to a generalized otitis externa. This is diagnosed by history and visual examination. The presence of a pressure equalization tube and otorrhea is diagnostic for this condition.

Cholesteatome is a cystic growth of squamous tissue into the ear canal or middle ear space. The cholesteatoma produces lysozymes that cause bony destruction, granulation and erythema. This condition is diagnosed by visual findings of squamous tissue invading the middle ear or ear canal.

Otitis media with perforation is a disease occurring in the area between the tympanic membrane and the inner ear, including the eustachian tube. Perforation of the tympanic membrane may present with a chronic or acute infection. Diagnosis is made by direct visual findings of a perforation of the tympanic membrane with purulent discharge and erythema of the canal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating otitis externa, comprising:
diagnosing an instance of otitis externa in a patient; and applying to the meatal tissues of the external ear of the patient, in a single application, a volume of a pharmaceutical composition within the range of about 0.1 ml to about 1.5 ml, wherein the pharmaceutical composition comprises an antifungal agent and a corticosteroid disposed in a viscous medium, wherein the corticosteroid is betamethasone or a betamethasone derivative, wherein the concentration of the corticosteroid is within the range of about 0.45 mg to about 0.9 mg per gram of the pharmaceutical composition, and wherein no subsequent dosage of the pharmaceutical composition is applied to the meatal tissues in treating the instance of otitis externa.

2. The method of claim 1, further comprising:
receiving a communication from a patient indicating a possible case of otitis externa;
instructing the patient to perform the applying step of claim 1; and
scheduling an office visit with the patient.

3. The method of claim 2, further includes instructing the patient to administer the pharmaceutical composition to the infected ear prior to the office visit.

4. The method of claim 1, wherein the corticosteroid is betamethasone.

5. The method of claim 1, wherein the composition has a pH of less than about 6.

6. The method of claim 1, wherein the pharmaceutical composition has a viscosity of greater than 200 centipoise.

7. The method of claim 1, wherein the pharmaceutical composition has a viscosity within the range of 20,000 to 64,000 centipoise.

8. The method of claim 1, wherein the pharmaceutical composition consists essentially of a corticosteroid.

9. The method of claim 1, wherein the pharmaceutical composition consists essentially of a corticosteroid and an antifungal agent.

10. The method of claim 1, wherein the pharmaceutical composition further comprises an antifungal agent, and wherein the antifungal agent is selected from the group consisting of natamycin, ciclopirox, clotrimazole, econazole, miconazole, nystatin, oxiconazole, terconazole, and tolnaftate.

11. The method of claim 1, wherein the pharmaceutical composition further comprises an antifungal agent, and wherein the antifungal agent is active against *aspergillus* fungi.

12. The method of claim 1, wherein the pharmaceutical composition further comprises an antifungal agent, and wherein the antifungal agent is active against candida fungi.

13. The method of claim 1, wherein the instance of otitis externa is swimmer's ear.

14. A method for treating swimmer's ear, comprising:
diagnosing an instance of swimmer's ear in a patient; and
applying to the meatal tissues of the external ear of the patient, in a single application, a volume of a pharmaceutical composition within the range of about 0.1 ml to about 1.5 ml, wherein the pharmaceutical composition comprises an antifungal agent and a corticosteroid disposed in a viscous medium;
wherein the corticosteroid is betamethasone or a betamethasone derivative, wherein the concentration of the corticosteroid is within the range of about 0.45 mg to about 0.9 mg per gram of the pharmaceutical composition, and wherein no subsequent dosage of the pharmaceutical composition is applied to the meatal tissues in treating the instance of otitis externa.

15. The method of claim 14, wherein the corticosteroid is betamethasone.

16. The method of claim 14, wherein the composition has a pH of less than about 6.

17. The method of claim 14, wherein the pharmaceutical composition has a viscosity of greater than 200 centipoise.

18. The method of claim 14, wherein the pharmaceutical composition has a viscosity within the range of 20,000 to 64,000 centipoise.

19. The method of claim 14, wherein the pharmaceutical composition consists essentially of a corticosteroid.

20. The method of claim 14, wherein the pharmaceutical composition consists essentially of a corticosteroid and an antifungal agent.

21. The method of claim 14, wherein the pharmaceutical composition further comprises an antifungal agent, and wherein the antifungal agent is selected from the group consisting of natamycin, ciclopirox, clotrimazole, econazole, miconazole, nystatin, oxiconazole, terconazole, and tolnaftate.

22. The method of claim 14, wherein the pharmaceutical composition further comprises an antifungal agent, and wherein the antifungal agent is active against aspergillus fungi.

23. The method of claim 14, wherein the pharmaceutical composition further comprises an antifungal agent, and wherein the antifungal agent is active against candida fungi.

24. The method of claim 14, wherein the concentration of the corticosteroid is within the range of about 0.45 mg to about 0.9 mg per gram of the pharmaceutical composition.

25. A method for treating swimmer's ear, comprising:
receiving a communication from a patient indicating a possible case of otitis externa;
instructing the patient to apply to the meatal tissues of their external ear, in a single application, a volume of a pharmaceutical composition within the range of about 0.1 ml to about 1.5 ml, wherein the pharmaceutical composition comprises an antifungal agent and a corticosteroid disposed in a viscous medium, wherein the corticosteroid is betamethasone or a betamethasone derivative, wherein the concentration of the corticosteroid is within the range of about 0.45 mg to about 0.9 mg per gram of the pharmaceutical composition; and
scheduling an office visit with the patient;
wherein no subsequent dosage of the pharmaceutical composition is applied to the meatal tissues in treating the possible case of otitis externa.

26. The method of claim 25, wherein instructing the patient to apply the pharmaceutical composition includes instructing the patient to administer the pharmaceutical composition to the infected ear prior to the office visit.

* * * * *